United States Patent [19]
Lee et al.

[11] Patent Number: 6,010,702
[45] Date of Patent: Jan. 4, 2000

[54] HERBAL DRUG COMPOSITION FOR THE PREVENTION AND TREATMENT OF DEMENTIA

[75] Inventors: Geon Mok Lee, Junrabuk-do; Byoung Soo Yu, 38-806, Hanshin-3cha Apt., Banpo-2dong, Seocho-ku, Seoul; Ki Young Kim, 104-904, Dong-Ah Apt., Busong-dong, Iksan-si, Junrabuk-do, all of Rep. of Korea

[73] Assignees: Geong Mok Lee; Byoung Soo Yu; Ki Young Kim; Young Soon Lee; Jang Hyun Jung, all of Rep. of Korea

[21] Appl. No.: 09/207,640

[22] Filed: Dec. 9, 1998

[51] Int. Cl.⁷ .................................................. A61K 35/78
[52] U.S. Cl. ........................................................ 424/195.1
[58] Field of Search ........................................... 424/195.1

[56] References Cited

U.S. PATENT DOCUMENTS

| | | | |
|---|---|---|---|
| 4,973,467 | 11/1990 | Sahley | 424/439 |
| 5,133,964 | 7/1992 | Kim | 424/195.1 |
| 5,164,184 | 11/1992 | Kim | 424/195.1 |
| 5,190,757 | 3/1993 | Kim | 424/195.1 |
| 5,225,203 | 7/1993 | Kim | 424/195.1 |
| 5,589,182 | 12/1996 | Tashiro et al. | 424/423 |

FOREIGN PATENT DOCUMENTS 2081089   2/1982   United Kingdom .

OTHER PUBLICATIONS

Benishin, C.G., Eur. J. Pharmacol., vol. 183(3), p. 931. Abstract, 1990.
Siegel, R.K., JAMA, vol. 241(15), p. 1614–1615, Apr. 1979.
Tsuda, T. et al., J. of Ethnopharmacology, vol. 15(3), p. 289–296, 1986.
Tsuda, T. et al., J. of Ethnopharmacology, vol. 17(3), p. 257–261, Sep. 1986.
Hiramatus, M. et al., IRCS J. Med. Sci., vol. 14(2), p. 189–190, Feb. 1986.
Hagino, N., Phytotherapy Research, vol. 7(6), p. 391–394, Nov. 1993.
J.E. Christie et al., "Physostigmine and Arecoline: Effects of Intravenous Infusions in Alzheimer Presenile Dementia", The British Journal of Psychiatry, vol. 138, pp. 46–50, Jan. 1981.
William Koopmans Summers et al., "Oral Tetrahydroaminoacridine in Long–Term Treatment of Senile Dementia, Alzheimer Type", The New England Journal of Medicine, vol. 315, pp. 1241–1245, Nov. 1986.
Ezio Giacobini, "Modulation of Brain Acetylcholine Levels with Cholinesterase Inhibitors as a Treatment of Alzheimer Disease", The Keio Journal of Medicine, vol. 36, No. 4, pp. 381–391, Oct. 1987.
George Ellman et al., "A New and Rapid Colorimetric Determination of Acetylcholinesterase Activity", Biochemical Pharmacology, vol. 7, pp. 88–95, 1961.

Primary Examiner—Jean C. Witz
Attorney, Agent, or Firm—Finnegan, Henderson, Farabow, Garrett & Dunner, L.L.P.

[57] ABSTRACT

This invention relates to an extract composition, prepared by a process comprising the steps of a) mixing about 30 to 80 weight parts of ginseng, about 6 to 24 weight parts of *Arisaematis rhizoma*, about 5 to 15 weight parts of *Gastrodiae rhizoma*, about 5 to 15 weight parts of *Acorus gramineus*, about 5 to 15 weight parts of *Ostericum Koreanum*, about 5 to 15 weight parts of *Bambusae caulis* in taenium, about 5 to 15 weight parts of *Bombycis corpus*, about 5 to 15 weight parts of *Ponciri fructus*, about 5 to 15 weight parts of Hoelen, about 5 to 15 weight parts of Pinelliae tuber, about 3 to 9 weight parts of *Aurantii nobilis pericarpium*, and about 3 to 9 weight parts of *Glycyrrhizae radix;* and b) extracting the mixture with thermally-purified water or alcohol. This extract composition can be used as the active ingredient in an herbal composition for the prevention and treatment of senile dementia.

10 Claims, No Drawings

HERBAL DRUG COMPOSITION FOR THE PREVENTION AND TREATMENT OF DEMENTIA

BACKGROUND OF THE INVENTION

1. Field of the Invention

This invention relates to an herbal drug composition for the prevention and treatment of senile dementia.

2. Description of the Related Art

Recently, many research studies have focused on Alzheimer's disease (AD), a senile dementia, in the biochemical, genetic and medical aspects. Dementia may refer to a general decline in all areas of cognitive function and intellectual ability which may significantly impair one's professional job, usual social activities or personal relations. More specifically, its main symptoms include a cognitive function impairment and various mental disorders in language, judgment and perceptive vasospastic ability as well as serious difficulty in acquisition of new technologies. Personality changes and emotional restlessness soon become apparent and ultimately lead to death. Dementia, which adversely affects the intrinsic activity of cerebrum, is a peculiar symptom associated with the fundamental disorders of brain induced by various factors. Due to loss of cerebral parenchyma, the brain was grossly shrunken in size and occasionally, a frontal lobe and temporal lobe are more severely shrunken, being accompanied by the expansion of ventricle in most cases. A large number of cerebral cortex cells, Purkinje cells in the cerebellum, or cells of the spinal cord shrink in size. The cause of Alzheimer's disease is unknown but it has been reported that from the autopsy of brain in dead patients with Alzheimer's disease, the level of neurotransmitter acetylcholine (ACh) was significantly reduced. Some drugs, which are still under research, aim to improve the cognitive function for the treatment of dementia and to alleviate the secondary mental disorders of dementia such as anxiety, delusion, irritation, insomnia and abnormal behavior. Some of the commercially available anti-dementia agents include COGNEX and ARICEPT, which were approved by Food and Drug Administration of U.S.A. These drugs inhibit the activity of acetylcholine esterase (AChE) acting mainly on the central nervous system, thus increasing the level of neurotransmitter acetylcholine for the prevention and treatment of dementia. Results of clinical studies using some drugs to inhibit the AChE activity indicate that improved memory enhancement was attained at synaptic clefts in the brain.

However, a majority of the conventional anti-dementia agents may produce serious cholinergic effects in the peripheral nerve with an extremely short half-life and serious side effects such as hepatotoxicity (ref: Br. J. Psychiatry, 138, 46, 1981). Further, Cognex (9-amino-1,2,3,4-tetrahydroacridine, THA), which has been widely used for the treatment of dementia, is effective in significant enhancement of cognitive ability in AD patients during oral administration (ref: N, Engl. J. Med., 315, 1241, 1986) but much adverse reactions such as tremor, dizziness and cytotoxicity have still encountered.

SUMMARY OF THE INVENTION

Under such circumstances, the inventor has made intensive studies to develop a novel drug having an inhibitory action on AChE with little adverse reaction and under the judgment that a drug containing some herbs may lessen any adverse reactions, screened some herbal components having an inhibitory action on AChE. As a result of repeated the efficacy screening and toxicity tests in a composition where some supplemental herbs are added to the basic herbal drugs having an inhibitory action on AChE, it has been confirmed that the herbal composition of this invention is quite effective in the prevention and treatment of dementia. In consequence, the inventor has completed this invention.

DETAILED DESCRIPTION OF THE INVENTION

This invention is explained in more detail as set forth hereunder:

This invention is characterized by an extract composition prepared by a process comprising the steps of a) mixing a mixture consisting of 30~80 weight parts of ginseng, 6~24 weight parts of *rhizoma Arisaematis*, 6~24 weight parts of *Gastrodiae Rhizoma*, 5~15 weight parts of *Acorus graminecus*, 5~15 weight parts of *Ostericum Koreanum*, 5~15 weight parts of *Bambusae Caulis* In Taeniam, 5~15 weight parts of *Bombycis Corpus*, 5~15 weight parts of *Ponciri Fructus*, 5~15 weight parts of Hoelen, 5~15 weight parts of Pinelliae Tuber, 3~9 weight parts of *Aurantii nobilis Pericarpium* and 3~9 weight parts of *Glycyrrhizae Radix*; and b) extracting the mixture with thermally-purified water for 6–8 hours or alcohol such as ethanol.

This invention is also characterized by a herbal drug composition for the prevention and treatment of senile dementia containing the above mentioned extract composition. The herbal drug composition may be formulated as extract liquid preparations, powders, pellets, granules, percolating agents, boiled agents, tablets, capsules or injectables dissolved in distilled water, if deemed necessary.

One cannot ascertain that each component of herbal drugs has an inhibitory action on AChE in their own nature but as a result of repeated comparative studies on some herbal drugs having various composition, a herbal drug having the above herbal components and composition rate has been confirmed to have the most optimal therapeutic efficacy.

When the herbal composition of this invention is orally administered for the desired therapeutic effect, an extract powder for an adult (60 kg) may be administered once at a dose of 7~10 g.

The construction and effect of this invention is explained in more detail based on the following manufacturing examples and experimental examples as set forth hereunder. However, these examples and experimental examples are the ones to further understand this invention and thus, the scope of this invention is not limited by these examples and experimental examples in any respects.

EXAMPLE 1

Preparation of Herbal Extract by Water

A mixture consisting of ginseng (50 g), *rhizoma Arisaematis* (15 g), *Gastrodiae Rhizoma* (15 g), *Acorus graminecus* (10 g), *Ostericum Koreanum* 10 g, *Bambusae Caulis* In Taeniam (10 g), *Bombycis Corpus* (10 g), *Ponciri Fructus* (10 g), Hoelen (10 g), Pinelliae Tuber (10 g) and *Aurantii nobilis Pericarpium* (6 g) and *Glycyrrhizae Radix* (6 g) was placed in 1 L of water, heated slowly and refluxed for 6~8 hours. Then, a liquid-phase solution was filtered off by a filter paper. Water in the remaining solution was completely removed from a freeze vapor drier to obtain a brown powder (12.2 g).

EXAMPLE 2

Preparation of Herbal Extract by Alcohol

A herbal mixture containing the same components and composition ratio as Example 1 was extracted 1 L of ethanol for 3 hours. Then, a liquid-phase solution was filtered off by a filter paper. Ethanol in the remaining solution was completely removed from a freeze vapor drier to obtain a brown powder (14.1 g).

EXPERIMENTAL EXAMPLE 1

Inhibitory Effect on AChE by an Extract of This Invention

To evaluate the inhibitory effect of an extract of this invention on AChE, each extract powder (0.25 g, 0.05 g and 0.1 g) prepared from Example 1 was added to an enzyme (1000 units) extracted from an electric eel (AChE: Sigma Cat. No. C-2888) dissolved in 1 ml PBS (phosphate buffer: 0.1M, pH 7.3). Based on a each AChE activity was measured by Ellman's coupled assay using an UV-visible spectrophotometer at 412 nm using a velocity constant factors of enzyme, Km (Micaelis constant), Vmax (maximum speed) and 5,5-dithio-bis-(2-nitrobenzoic acid: DTNB) as a coupling agent. As shown in the following table 1, the inhibitory effect of an extract of this invention on AChE showed that at doses of 0.5 mg/ml and 1.0 mg/ml, the extract of this invention induced decrease in the enzymatic activity by 29.5% and 50.3%, respectively.

TABLE 1

| Amount of herbal drug (mg/ml) | Initial rate (Au/s) | Loss of enzymatic activity (%) |
| --- | --- | --- |
| 0 | $2.919 \times 10^{-3}$ | 0 |
| 0.25 | $2.660 \times 10^{-3}$ | 8.7 |
| 0.5 | $2.123 \times 10^{-3}$ | 29.5 |
| 1.0 | $1.450 \times 10^{-3}$ | 50.3 |

It can be safely said that the inhibitory activity (50.3%) of the herbal extract of this invention on AChE is quite remarkable, in consideration of the fact that THA (brandname: Cognex) exhibits about an inhibitory action on AChE by 40% at maximum (ref: Keio J. Med., 36, 381, 1987).

EXPERIMENTAL EXAMPLE 2

Inhibitory Action on AChE in the Brain of Rats

Through the in vivo study to evaluate the inhibitory effect of an extract of this invention on AChE, 20-week-old rats were divided into 2 groups (treatment and control groups) consisting of 7 individuals each prior to commencement of administration. A solution containing 6.3 g of powder, so prepared from Example 1, dissolved in 100 ml distilled water was orally administered to the treatment group at a daily dose of 3 ml for consecutive days, while no medication was given to the control group. After 10 days, the brain of rats was removed to weigh the total weight of brain. Then, 5 ml PBS (0.1M, pH 7.3) was added to the brain, crushed completely, and stirred slowly for 3~5 hours. 2 ml PBS (0.1M, pH 7.3) was further added to the solution of brain cell for stirring, centrifuged (Hettich Rotina 48R) at 1000 rpm at 4° C. for 10 minutes centrifuge and purified by a filter (CAMEO 25ES nitrocellulose pore size: 0.45 mm)

The AChE activity of rat brain was measured by Ellman's coupled assay (ref: Ellman, G. L., Biochem. Pharmacol., 7, 88, 1961) using an UV-visible spectrophotometer at 412 nm. Hence, the enzymatic reaction rate on all substrates at the intervals of time was calculated by Michaelis-Menten equation. The purified brain was incubated in a 1 ml quartz cuvette containing 790 ul of PBS (0.1M, pH 7.3), 60 ul substrate in 5 ml solution (ATcH: acethylthiocoline) and 120 ul DTNB (dithionitrobenzoic acid) in 5 mM solution as a coupling agent for about 3 minutes and then, each 10 ul of brain solution extracted from the treatment and control groups was added to the quartz cuvette for assessment of AChE activity, as shown in the following table 2.

TABLE 2

| AChF activity of extracted brain in rats | | |
| --- | --- | --- |
| Classification | Mean initial rate of AChE (Au/s) | Loss of AChE activity (%) |
| Normal rats | $3.100 \times 10^{-3}$ | 0 |
| Rats with oral administration of herbal extracts (3 ml/day) | $2.384 \times 10^{-3}$ | 23.1 |

From the above in vivo test, it was noted that when the herbal extract of this invention was administered to rats for 10 consecutive days, the AChE activity was reduced by 23.1% compared with rats having no medication. Thus, it has proven that the herbal extract of this invention has an inhibitory action on AChE.

EXPERIMENTAL EXAMPLE 3

Increasing Concentration of Neurontransmitter Acetylcholine in Rats Brain

Female Spague-Dawley rats (pyrogen test free) at three weeks of age were purchased and housed at 18° C. in a light/dark cycle to grow 20-week-old rats (250~350 g) for use in this study. A herbal extract prepared from Example 1 of this invention was orally administered to each experimental rats consisting of 7 individuals for 10 days in the same manner as Experimental example 2. After 10 days, all rats were necropsied and the weight of brain was measured. The brain cells were homogenized by 10 ml PBS (phosphate buffer: 0.1M, pH 7.3) containing 0.2% tripton X-100 and centrifuged (1000 rpm) at 4° C. to isolate acetylcholine from the brain cell solution. The acetylcholine, so isolated, was assayed by HPLC equpped with an electrode detector. Some standard graphs of acetylcholine at accurate concentrations were prepared to analyze each sample of 20 ul extracted from the rats brain under the same conditions (flow rate: 10 ml/min, detection scope: 3,9062 nA, solvent: 0.1M PBS at pH 7.3). When each group consisting of 7 rats was given an herbal extract to their brains at the intervals of time to compare their level of acetylcholine, so biochemically isolated, with that of normal rats, the results were shown in the following table 3.

TABLE 3

| Day | Amount of acetylcholine($\mu$M) | Increasing rate of acetylcholine(%) | No. of rats |
| --- | --- | --- | --- |
| 0 (normal rats) | 107.7 | 0 | 7 |
| 5 | 139.6 | 29.6 | 7 |
| 10 | 193.4 | 79.6 | 7 |

The above results indicated that the actual concentration increase of neurontransmitter acetylcholine was observed in rats with an herbal extract of this invention, thus reflecting the actual inhibitory effect of such herbal extract on AChE in the body. The concentration of acetylcholine was increased by 29.6% and 79.6% after 5-day and 10-day administration of herbal extract, respectively. The herbal extract of this invention has more 5-fold potent inhibitory action on AChE than some other natural products disclosed in the Japanese Patent No. 25760, while having at least 3-fold potent inhibitory action on AChE than synthetic anti-dementia agents for the prevention and treatment of dementia (ref: Keio J. Med., 36, 381, 1987). In particular, the naturally occurring herbal drugs used for this studies, which have been clinically used for several thousand years as other purposes of use, has little adverse reactions which have encountered in the medication using the conventional drugs (ref: Experimental example 11).

EXPERIMENTAL EXAMPLE 4

Preparation of Pellet Form and its Efficacy Screening

Each 1 g of a dried pellet form prepared from the mixing of 5 g of honey with 100 g of herbal powder, so prepared from Example 1, was dissolved in water (10 ml) every day for its oral administration to 20-week-old Spague-Dawley rats for 10 consecutive days. After 10 days, the activity of AChE and acetylcholine level in brain was measured in the same manner as Experimental examples 2 and 3. The results of this experiment revealed that the pellet form had the same inhibitory action on AChE with increasing concentration of acetylcholine, as in Experimental examples 2 and 3).

EXPERIMENTAL EXAMPLE 5

Preparation of Powder Form and its Efficacy Screening 100 g of herbal powder, so prepared from Example 1, was finely pulverized, passed through No. 18 sieve (850 ug), followed by the addition of lactose (200 g) as an excipient to prepare a powder form. Each 0.7 g of the powder form was dissolved in water (10 ml) every day for its oral administration to 20-week-old Spague-Dawley rats for 10 consecutive days. After 10 days, the activity of AChE and acetylcholine level in brain was measured in the same manner as Experimental examples 2 and 3. The results of this experiment revealed that the powder form had the same inhibitory action on AChE with increasing concentration of acetylcholine, as in Experimental examples 2 and 3).

EXPERIMENTAL EXAMPLE 6

Preparation of Tablet Form and its Efficacy Screening 100 g of herbal powder, so prepared from Example 1, was mixed with 25 g of lactose and 5 g of starch and with the addition of talc (5 g), the mixture was formulated by a tabletting machine to prepare a film-coating tablet. Each 0.7 g of the tablet form was dissolved in water (10 ml) every day for its oral administration to 20-week-old Spague-Dawley rats for 10 consecutive days. After 10 days, the activity of AChE and acetylcholine level in brain was measured in the same manner as Experimental examples 2 and 3. The results of this experiment revealed that the tablet form had the same inhibitory action on AChE with increasing concentration of acetylcholine, as in Experimental examples 2 and 3).

EXPERIMENTAL EXAMPLE 7

Preparation of Granule Form and its Efficacy Screening 100 g of herbal powder, so prepared from Example 1, was mixed with 25 g of lactose and 5 g of starch, passed through a sieve (No. 12-45) to prepare a granule form. Each 1.0 g of the granule form was dissolved in water (10 ml) every day for its oral administration to 20-week-old Spague-Dawley rats for 10 consecutive days. After 10 days, the activity of AChE and acetylcholine level in brain was measured in the same manner as Experimental examples 2 and 3. The results of this experiment revealed that the granule form had the same inhibitory action on AChE with increasing concentration of acetylcholine, as in Experimental examples 2 and 3).

EXPERIMENTAL EXAMPLE 8

Preparation of Capsule Form and its Efficacy Screening 100 g of herbal powder, so prepared from Example 1, was filled into a capsule (No. 3, 0.3 ml). Each 0.7 g of the capsule form was dissolved in water (10 ml) every day for its oral administration to 20-week-old Spague-Dawley rats for 10 consecutive days. After 10 days, the activity of AChE and acetylcholine level in brain was measured in the same manner as Experimental examples 2 and 3. The results of this experiment revealed that the capsule form had the same inhibitory action on AChE with increasing concentration of acetylcholine, as in Experimental examples 2 and 3).

EXPERIMENTAL EXAMPLE 9

Preparation of Percolating Agent and its Efficacy Screening

A herbal mixture having the same components and composition ratio as Example 1 was finely pulverized and with the addition of purified water (200 ml), precipitated for 3 hours. A thermally-purified water (700 ml) was added and mixed to the resulting solution several times, cooled and filtered by a cotton. 50 g of honey was further added to the solution. Each 3 ml of the percolating agent was orally administered to 20-week-old Spague-Dawley rats for 10 consecutive days. After 10 days, the activity of AChE and acetylcholine level in brain was measured in the same manner as Experimental examples 2 and 3. The results of this experiment revealed that the percolating agent had the same inhibitory action on AChE with increasing concentration of acetylcholine, as in Experimental examples 2 and 3).

EXPERIMENTAL EXAMPLE 10

Preparation of Boiled Agent and its Efficacy Screening

Purified water (900 ml) was added and mixed several times to a herbal mixture having the same components and composition ratio as Example 1, heated for more than 30 mins and filtered off in warm state. 50 g of honey was added to the resulting solution as a flavoring agent. Each 3 ml of the boiled agent was orally administered to 20-week-old Spague-Dawley rats for 10 consecutive days. After 10 days, the activity of AChE and acetylcholine level in brain was measured in the same manner as Experimental examples 2 and 3. The results of this experiment revealed that the percolating agent had the same inhibitory action on AChE with increasing concentration of acetylcholine, as in Experimental examples 2 and 3).

EXPERIMENTAL EXAMPLE 11

Liver Function Test of Rats in Serum 20-week-old Spague-Dawley rats were divided into a placebo group (8 rats) and a treatment group (9 rats). 500 mg of herbal powder, so prepared from Example 1, was dissolved in purified water (100 ml) and then, each 3 ml of the solution was orally administered to the treatment group at 10 o'clock every morning for 10 consecutive days. After 10 days, the animals were sacrificed to collect the blood samples. The blood samples were centrifuged at 1500 rpm at 4° C. for 10 mins to separate the sera. Then, the liver function test on such sera was performed according to the conventional method. As revealed in the following table 4, it was noted that both groups had nearly similar levels in AST, ALT, ALP and BUN, thus reflecting that the herbal drug of this invention had no primary hepatotoxicity.

TABLE 4

Concentration of various parameters in blood

| Group | AST(IU/l) | ALT(IU/l) | ALP(IU/l) | BUN(IU/l) | n |
|---|---|---|---|---|---|
| Placebo | 171.3 ± 26.6 | 56.4 ± 14.8 | 433.3 ± 181.3 | 21.2 ± 3.0 | 8 |
| Treatment | 112.2 ± 38.1 | 58.1 ± 14.8 | 421.3 ± 101.1 | 22.3 ± 2.3 | 9 |

What is claimed is:

1. An extract composition prepared by a process comprising the steps of a) mixing a mixture consisting of 30~80 weight parts of ginseng, 6~24 weight parts of *rhizoma Arisaematis*, 6~24 weight parts of *Gastrodiae Rhizoma*, 5~15 weight parts of *Acorus graminecus*, 5~15 weight parts of *Ostericum Koreanum*, 5~15 weight parts of *Bambusae Caulis* In Taeniam, 5~15 weight parts of *Bombycis Corpus*, 5~15 weight parts of *Ponciri Fructus*, 5~15 weight parts of Hoelen, 5~15 weight parts of *Pinelliae Tuber*, 3~9 weight parts of *Aurantii nobilis Pericarpium* and 3~9 weight parts of *Glycyrrhizae Radix;* and b) extracting the mixture with thermally-purified water or alcohol.

2. The extract according to claim 1, wherein said alcohol is ethanol.

3. The extract according to claim 1, wherein the extracting step with thermally-purified water is carried out for 6~8 hours.

4. A herbal drug composition for inhibiting the activity of acetylcholinesterase in the brain comprising an extracted mixture of about 30 to 80 weight parts of ginseng, about 6 to 24 weight parts of *rhizoma Arisaematis*, about 5 to 15 weight parts of *Gastrodiae rhizoma*, about 5 to 15 weight parts of *Acorus gramineus*, about 5 to 15 weight parts of *Ostericum Koreanum*, about 5 to 15 weight parts of *Bambusae caulis* in taenium, about 5 to 15 weight parts of *Bombycis corpus*, about 5 to 15 weight parts of *Ponciri fructus*, about 5 to 15 weight parts of hoelen, about 5 to 15 weight parts of Pinelliae tuber, about 3 to 9 weight parts of *Aurantii nobilis pericarpium*, and about 3 to 9 weight parts of *Glycyrrhizae radix*.

5. The herbal drug composition according to claim 4, wherein the composition was extracted with an alcohol.

6. The herbal drug composition according to claim 4, wherein the composition was extracted with thermally-purified water for a period of about 6 to about 8 hours.

7. The herbal drug composition according to claim 1, wherein the composition is in a suitable dosage form.

8. The herbal drug composition according to claim 7, wherein the dosage form is selected from the group consisting of a liquid preparation, a tablet, a capsule, a powder, an injectable preparation, pellets and granules.

9. A process for preparing a herbal drug extract, wherein the process comprises the steps of (a) mixing a composition of about 30 to 80 weight parts of ginseng, about 6 to 24 weight parts of *rhizoma Arisaematis*, about 5 to 15 weight parts of *Gastrodiae rhizoma*, about 5 to 15 weight parts of *Acorus gramineus*, about 5 to 15 weight parts of *Ostericum Koreanum*, about 5 to 15 weight parts of *Bambusae caulis* in taenium, about 5 to 15 weight parts of *Bombycis corpus*, about 5 to 15 weight parts of *Ponciri fructus*, about 5 to 15 weight parts of hoelen, about 5 to 15 weight parts of *Pinelliae tuber*, about 3 to 9 weight parts of *Aurantii nobilis pericarpium*, and about 3 to 9 weight parts of *Glycyrrhizae radix* with purified water;

(b) heating the composition of step (a) for at least 30 minutes; and (c) filtering the heated composition of step (b) to yield a boiled herbal drug extract.

10. A process for preparing a herbal drug extract, wherein the process comprises the steps of:

(a) pulverizing composition of about 30 to 80 weight parts of ginseng, about 6 to 24 weight parts of *rhizoma Arisaematis*, about 5 to 15 weight parts of *Gastrodiae rhizoma*, about 5 to 15 weight parts of *Acorus gramineus*, about 5 to 15 weight parts of *Ostericum Koreanum*, about 5 to 15 weight parts of *Bambusae caulis* in taenium, about 5 to 15 weight parts of *Bombycis corpus*, about 5 to 15 weight parts of *Ponciri fructus*, about 5 to 15 weight parts of hoelen, about 5 to 15 weight parts of Pinelliae tuber, about 3 to 9 weight parts of *Aurantii nobilis pericarpium*, and about 3 to 9 weight parts of *Glycyrrhizae radix;*

(b) mixing the composition of step (a) with purified water; and (c) precipitating the composition of step (b) for about three hours to yield a percolated herbal drug extract.

* * * * *

UNITED STATES PATENT AND TRADEMARK OFFICE
CERTIFICATE OF CORRECTION

PATENT NO.: 6,010,702

DATED: January 4, 2000

INVENTOR(S): Geon Mok Lee; Byoung Soo Yu; Ki Young Kim

It is certified that an error appears in the above-identified patent and that said Letters Patent is hereby corrected as shown below:

On the Title Page, insert item --[30] Foreign Application Priority Data
May 14, 1998 [KR] Rep. of Korea.............98-017429--.

On the Title Page, item [75], after "Inventors: Geon Mok Lee," insert --401-906, Hyundai-4cha Apt., Mohyun-dong, Iksan-si,--.

In claim 1, column 7, line 29, "In" should read --in--.

Signed and Sealed this

Third Day of April, 2001

*Attest:*

NICHOLAS P. GODICI

*Attesting Officer*   Acting Director of the United States Patent and Trademark Office